(12) United States Patent
Voskoboynikov et al.

(10) Patent No.: US 11,130,720 B2
(45) Date of Patent: *Sep. 28, 2021

(54) PROCESSES FOR METHYLATION OF AROMATICS IN AN AROMATICS COMPLEX

(71) Applicant: UOP LLC, Des Plaines, IL (US)

(72) Inventors: Timur V. Voskoboynikov, Arlington Heights, IL (US); Deng-Yang Jan, Elk Grove Village, IL (US); John Q. Chen, Morton Grove, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,515

(22) Filed: Mar. 23, 2018

(65) Prior Publication Data

US 2019/0292117 A1    Sep. 26, 2019

(51) Int. Cl.
| | |
|---|---|
| C07C 2/86 | (2006.01) |
| B01J 29/70 | (2006.01) |
| C07C 6/12 | (2006.01) |
| C07C 15/08 | (2006.01) |

(52) U.S. Cl.
CPC .......... *C07C 2/864* (2013.01); *B01J 29/7038* (2013.01); *C07C 6/126* (2013.01); *C07C 15/08* (2013.01); *B01J 2229/16* (2013.01); *B01J 2229/34* (2013.01); *B01J 2229/36* (2013.01); *B01J 2229/37* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 4,761,513 A | 8/1988 | Steacy | |
| 4,929,358 A | 5/1990 | Koenitzer | |
| 5,171,915 A | 12/1992 | Forbus et al. | |
| 5,349,114 A | 9/1994 | Lago et al. | |
| 5,477,184 A | 12/1995 | Uda et al. | |
| 5,488,194 A | 1/1996 | Beck et al. | |
| 5,939,597 A | 8/1999 | Dessau et al. | |

(Continued)

FOREIGN PATENT DOCUMENTS

| | | |
|---|---|---|
| CN | 1245477 A | 2/2000 |
| CN | 1721378 A | 1/2006 |

(Continued)

OTHER PUBLICATIONS

Schwanke et al. Lamellar MWW-Type Zeolites: Toward Elegant Nanoporous Materials. Applied Science. 2018. pp. 1-15 (Year: 2018).*

(Continued)

*Primary Examiner* — Philip Y Louie
*Assistant Examiner* — Alyssa L Cepluch

(57) ABSTRACT

This present disclosure relates to processes for methylation of aromatics in an aromatics complex for producing a xylene isomer product. More specifically, the present disclosure relates to a process for producing para-xylene by the selective methylation of toluene and/or benzene in an aromatics complex using mild reaction conditions, namely a combination of low temperatures and elevated pressures using a zeolite with lower number of external acid sites.

18 Claims, 1 Drawing Sheet

(56) References Cited

U.S. PATENT DOCUMENTS

| | | | |
|---|---|---|---|
| 5,939,797 | A | 8/1999 | Konno et al. |
| 6,642,426 | B1 | 11/2003 | Johnson et al. |
| 6,740,788 | B1 | 5/2004 | Maher et al. |
| 6,756,030 | B1 | 6/2004 | Rohde et al. |
| 7,060,864 | B2 | 6/2006 | Ghosh et al. |
| 7,268,267 | B2 | 9/2007 | Jan et al. |
| 7,446,069 | B2 | 11/2008 | Ghosh et al. |
| 7,638,667 | B2 * | 12/2009 | Jan .............. B01J 29/06 585/467 |
| 7,663,010 | B2 * | 2/2010 | Levin ............ C07C 6/126 585/470 |
| 7,812,208 | B2 | 10/2010 | Cheng et al. |
| 7,982,084 | B1 * | 7/2011 | Moscoso ........ C07C 2/12 208/111.01 |
| 7,985,886 | B1 | 7/2011 | Jan et al. |
| 8,399,727 | B2 | 3/2013 | Lattner et al. |
| 8,450,232 | B2 * | 5/2013 | Yeh .............. B01J 29/06 502/60 |
| 9,249,067 | B2 | 2/2016 | Vincent et al. |
| 9,302,953 | B2 | 4/2016 | Molinier et al. |
| 9,446,961 | B2 | 9/2016 | Johnson et al. |
| 9,783,462 | B2 | 10/2017 | Ghosh et al. |
| 2004/0015027 | A1 | 1/2004 | Iaccino et al. |
| 2004/0097769 | A1 | 5/2004 | Ou et al. |
| 2004/0199036 | A1 | 10/2004 | Jan et al. |
| 2005/0027151 | A1 | 2/2005 | Ghosh et al. |
| 2005/0143613 | A1 | 6/2005 | Dakka et al. |
| 2009/0187056 | A1 | 7/2009 | Chewter et al. |
| 2009/0253949 | A1 | 10/2009 | Ghosh et al. |
| 2011/0243838 | A1 | 10/2011 | Moscoso et al. |
| 2013/0137910 | A1 | 5/2013 | Vincent et al. |
| 2013/0324779 | A1 | 12/2013 | Heeter et al. |
| 2014/0206909 | A1 * | 7/2014 | Calaresu ........ C07C 2/864 568/798 |
| 2014/0213840 | A1 * | 7/2014 | Helton ........... C07C 2/862 585/466 |
| 2014/0296598 | A1 | 10/2014 | Heeter et al. |
| 2014/0336436 | A1 | 11/2014 | Bender et al. |
| 2015/0073187 | A1 | 3/2015 | Ghosh et al. |
| 2015/0376086 | A1 * | 12/2015 | Tinger ............ B01J 19/2445 585/314 |
| 2016/0024393 | A1 | 1/2016 | Beech, Jr. et al. |
| 2016/0046544 | A1 | 2/2016 | Molinier et al. |
| 2016/0060542 | A1 | 3/2016 | Sugita et al. |
| 2017/0368540 | A1 * | 12/2017 | Mettler ........... C07C 2/62 |
| 2018/0099913 | A1 | 4/2018 | Chen et al. |
| 2018/0099915 | A1 * | 4/2018 | Chen ............. C07C 2/864 |
| 2018/0251413 | A1 | 9/2018 | Loveless et al. |
| 2019/0359542 | A1 | 11/2019 | Detjen et al. |

FOREIGN PATENT DOCUMENTS

| | | | |
|---|---|---|---|
| CN | 1775715 | A | 5/2006 |
| CN | 103121912 | A | 5/2013 |
| CN | 103588612 | A | 2/2014 |
| CN | 105439790 | A | 3/2016 |
| CN | 105503508 | A | 4/2016 |
| CN | 105503509 | A | 4/2016 |
| CN | 105646132 | A | 6/2016 |
| EP | 249913 | B1 | 4/1991 |
| GB | 1474065 | A | 5/1977 |
| JP | 58199044 | A | 11/1983 |
| JP | 62063528 | A | 3/1987 |
| JP | H10502908 | A | 3/1998 |
| JP | 2007533586 | A | 11/2007 |
| JP | 2008544986 | | 12/2008 |
| JP | 2013523583 | A | 6/2013 |
| JP | 2014531390 | A | 11/2014 |
| KR | 20060109503 | A | 10/2006 |
| RU | 2083730 | C1 | 7/1997 |
| WO | 1995013998 | A1 | 5/1995 |
| WO | 2000040527 | A1 | 7/2000 |
| WO | 2004074219 | A2 | 9/2004 |
| WO | 2011123337 | A2 | 10/2011 |
| WO | 2016081110 | A1 | 5/2016 |
| WO | 2017105848 | A1 | 6/2017 |
| WO | 2017172067 | A2 | 10/2017 |
| WO | 2018067281 | A1 | 4/2018 |

OTHER PUBLICATIONS

Wu et.al., Selective formation of p-xylene with disproportionation of toluene over MCM-22 catalysts, Microporous and Mesoporous Materials (ISSN 1387-1811) V22 N.1-3 343-56 (Jun. 17, 1998), v 22, n 1-3, p. 343-56, Jun. 17, 1998.

Das et.al., Aromatization of C4-C6 hydrocarbons to benzene, toluene and para xylene over pore size controlled ZnO—HZSM-5 zeolite, Catalysis Society of India 13th National Symposium & Silver Jubilee Symposium (Dehradun Apr. 2-4, 1997) Studies in Surface Science and Catalysis V113 447-53 (1998), 1998.

Ducarme et.al., ZSM-5 and ZSM-11 Zeolites: Influence of Morphological and Chemical Parameters on Catalytic Selectivity and Deactivation, Applied Catalysis, 17 (1985) 175-184. Elsevier Science Publishers B.V., Amsterdam.

International Search Report from corresponding PCT application No. PCT/US2019/023673, dated Jun. 20, 2019.

Bajus, et al., Steam Cracking of Hydrocarbons-4. An Analysis of the High-Boiling (Polynuclear Aromatic Hydrocarbon) Products from (Steam Cracking of) Naphtha in a Quartz (Tubular) Reactor, Ind. Eng. Chem., Prod. Res. Dev. V19, N.4, 564-68 (Dec. 1980).

Adebajo et al, Methylation of benzene with methanol over zeolite catalysts in a low pressure flow reactor, Catalysis Today, v. 63, n 2-4, p. 471-478, Dec. 25, 2000.

Adebajo et al, The contribution of the methanol-to-aromatics reaction to benzene methylation over ZSM-5 catalysts, Catalysis Communications, v. 4, n 2, p. 71-76, Feb. 2003.

Ahn, et al., Methanol usage in toluene methylation with medium and large pore zeolites, ACS Catalysis, v. 3, n 5, p. 817-825, May 3, 2013.

Tangestanifard et al., Methylation of toluene with methanol in sub/supercritical toluene using H-beta zeolite as catalyst, Journal of Supercritical Fluids, v. 113, p. 80-88, Jul. 2016.

International Search Report and Written Opinion from corresponding PCT Application No. PCT/US2018/064022, dated Mar. 21, 2019.

PCT Search report dated Mar. 15, 2018 for corresponding PCT application No. PCT/US2017/065535.

Chen et al., Continuous liquid phase acylation of toluene over HBEA zeolite: Solvent effects and origin of the deactivation, Journal of Molecular Catalysis A: Chemical, v. 396, 231-238, Jan. 1, 2015.

Hu et al., The effect of Si/Al ratio on the catalytic performance of hierarchical porous ZSM-5 for catalyzing benzen alkylation with methanol, Catalysis Science and Technology, v. 6, n 8, p. 2647-2652, Apr. 21, 2016.

Chareonpanich, et al., The hydrocracking of aromatic hydrocarbons over USY-zeolite, Energy & Fuels (ISSN 0887-0624) V10 N.4, 927-31 (Jul. 1996).

Chareonpanich, et al., Remarkable increase of BTX yield by zeolite catalyst in the hydrocracking of coal volatile matter, Coal. Sci. Technol., 24 (Coal Sciene, vol. 2) 1483-6 (1995) Chemical Abstracts (ISSN 0009-2258) Abstr. No. 150548 V124 N.12, 1995, p. 1483-1486.

International Preliminary Report on Patentability for PCT/US2017/065535, dated Jun. 25, 2019.

International Preliminary Report for PCT application No. PCT/US2019/023673, dated Sep. 29, 2020.

International Preliminary Report for PCT application No. PCT/US2017/064022, dated Jun. 9, 2019.

Tseng-Chang Tsai et al., Disproportionation and transalkylation of alkylbenzenes over zeolite catalysts, Applied Catalysis A: General 181 (1999) 355-398.

* cited by examiner

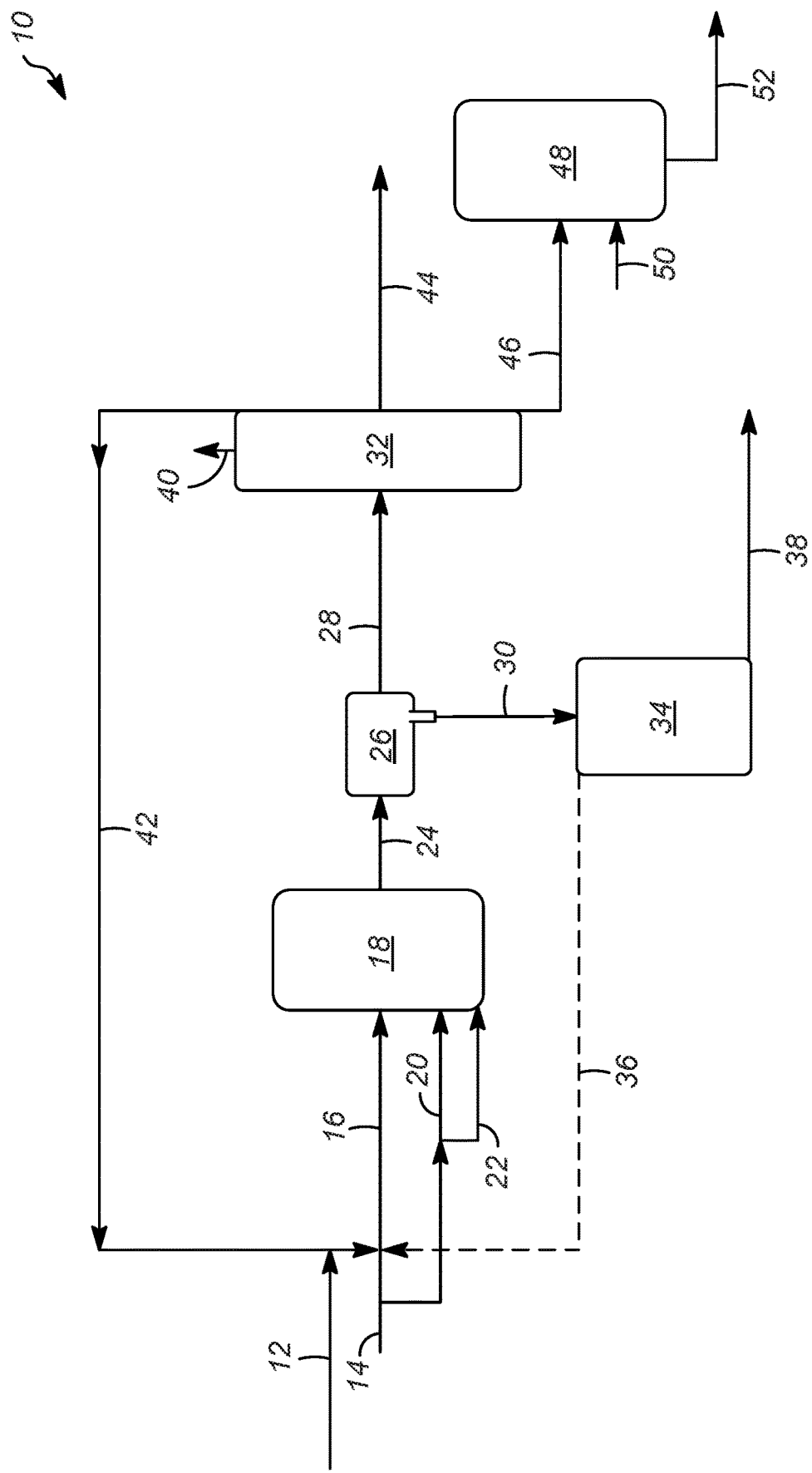

PROCESSES FOR METHYLATION OF AROMATICS IN AN AROMATICS COMPLEX

FIELD

This present disclosure relates to processes for methylation of aromatics in an aromatics complex for producing a xylene isomer product. More specifically, the present disclosure relates to a process for producing para-xylene by the selective methylation of toluene and/or benzene in an aromatics complex using mild reaction conditions, namely a combination of low temperatures and moderately elevated pressures using a zeolite with lower number of external acid sites.

BACKGROUND

High selectivity in toluene methylation is a key for the process economics. In low-temperature version of toluene methylation the para-xylene to xylene ratio is generally between 40-60%, and some undesired byproducts also present. High selectivity greatly improves the competitiveness of virtually all processes, including low temperature toluene methylation. It has been discovered that certain acid sites, located most likely on the external surface of MWW zeolites (including MCM-22, MCM-49, UZM-8, UZM-37), have undesired effect on the selectivity. For example, they likely to contribute to para-xylene to meta-xylene isomerization, thus lowering the para-xylene to xylene ratio of the product. It has been known from prior art that these undesired sites can be removed by using Al-chelating agents, including but not limited to, organic acids (oxalic, citric, tartaric, EDTA, etc), ammonium hexafluorosilicate (AFS), inorganic acids such as nitric acid, as well as steaming.

Accordingly, it is desirable to provide improved methods for methylation of aromatic compounds such as toluene and benzene in an aromatics complex. Further, it is desirable to provide a cost-effective method for toluene and/or benzene methylation which operates using mild reaction conditions, namely a combination of low temperatures and elevated pressures using a zeolite with lower number of external acid sites.

SUMMARY

The present subject matter relates to processes for toluene and/or benzene methylation in an aromatics complex for producing xylene isomer. More specifically, the present disclosure relates to processes for toluene methylation under mild reaction conditions, namely a combination of low temperatures and elevated pressures using a zeolite with lower number of external acid sites. The acid sites are removed using ammonium hexafluorosilicate (AFS) on calcined, or template-free zeolite. Also, the original (i.e. before treatment) zeolite preferably should have a low silica to alumina ratio.

In the foregoing, all temperatures are set forth in degrees Celsius and all parts and percentages are by weight, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

BRIEF DESCRIPTION OF THE DRAWING

The FIGURE illustrates a process for toluene methylation under mild reaction conditions, namely a combination of low temperatures and moderately elevated pressures.

Definitions

As used herein, the term "stream" can include various hydrocarbon molecules and other substances.

As used herein, the term "stream", "feed", "product", "part" or "portion" can include various hydrocarbon molecules, such as straight-chain and branched alkanes, naphthenes, alkenes, alkadienes, and alkynes, and optionally other substances, such as gases, e.g., hydrogen, or impurities, such as heavy metals, and sulfur and nitrogen compounds. Each of the above may also include aromatic and non-aromatic hydrocarbons.

As used herein, the term "overhead stream" can mean a stream withdrawn at or near a top of a vessel, such as a column.

As used herein, the term "bottoms stream" can mean a stream withdrawn at or near a bottom of a vessel, such as a column.

Hydrocarbon molecules may be abbreviated C1, C2, C3, Cn where "n" represents the number of carbon atoms in the one or more hydrocarbon molecules or the abbreviation may be used as an adjective for, e.g., non-aromatics or compounds. Similarly, aromatic compounds may be abbreviated A6, A7, A8, An where "n" represents the number of carbon atoms in the one or more aromatic molecules. Furthermore, a superscript "+" or "−" may be used with an abbreviated one or more hydrocarbons notation, e.g., C3+ or C3−, which is inclusive of the abbreviated one or more hydrocarbons. As an example, the abbreviation "C3+" means one or more hydrocarbon molecules of three or more carbon atoms.

As used herein, the term "unit" can refer to an area including one or more equipment items and/or one or more sub-zones. Equipment items can include, but are not limited to, one or more reactors or reactor vessels, separation vessels, distillation towers, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top or overhead pressure is the pressure of the overhead vapor at the vapor outlet of the column. The bottom temperature is the liquid bottom outlet temperature. Net overhead lines and net bottoms lines refer to the net lines from the column downstream of any reflux or reboil to the column unless otherwise shown. Stripping columns may omit a reboiler at a bottom of the column and instead provide heating requirements and separation impetus from a fluidized inert media such as steam.

As depicted, process flow lines in the drawings can be referred to interchangeably as, e.g., lines, pipes, feeds, gases, products, discharges, parts, portions, or streams.

The term "passing" means that the material passes from a conduit or vessel to an object.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The description of the apparatus of this invention is presented with reference to the attached FIGURE. The FIG. 1s a simplified diagram of the preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The various embodiments described herein relate to processes for toluene and or benzene methylation in an aromatics complex for producing xylene isomer. As shown in the FIGURE, a process 10 comprises of a first feed stream 12 comprising toluene and a second feed stream 14 comprising methanol. The first feed stream 12 and the second feed stream 14 are combined and pass to a reaction zone 18 via line 16. Additional methanol streams may be fed to the reaction zone 18 via lines 20 and 22. It is also contemplated that additional methanol streams may also be added to the reaction zone 18. Passing multiple methanol streams to the reaction zone 18 maximizes the toluene to methanol ratio and minimizes temperature rise due to reaction exotherm. The reaction zone 18 may comprise multiple reactors. The reaction zone 18 may comprise only one reactor or one reactor with interstage injection points to control the reactor exotherm, or the reaction zone 18 may comprise up to four reactors. The reaction zone 18 operates at a temperature of about 200° C. to about 400° C. The reaction zone 18 operates at a pressure of about 15 psig to about 400 psig.

The reaction zone product stream 24 exits the reaction zone 18 and passes to the separator 26. The reaction zone product stream 24 comprises toluene, para-xylene, and water. The separator 26 separates stream 24 into stream 28 and stream 30. Stream 28 passes to a stripper 32. Stream 30 passes to a methanol stripper 34 which provides a methanol recycle stream 36 to the reaction zone 18. The methanol stripper product stream 38 exits the methanol stripper 34 and goes to waste water treating. Sending the methanol to the methanol stripper 34 purifies the product methanol that is recycled, which is favorable for lower methanol conversions.

The stripper 32 produces an overhead stream 40 comprising vent to fuel gas, an overhead stream 42 comprising toluene and benzene that is recycled back to the first feed stream 12, a side cut 44 comprising para-xylene, toluene, ortho-xylene, meta-xylene, and some C9-C10, and a bottom stream 46 comprising C9+, which includes diphenylmethanes. The bottoms stream 46 is passed to a transalkylation unit 48 which also receives a stream 50 comprising benzene and C9+ as well as potentially toluene. The tranalkylation unit comprises a transalkylation catalyst which comprises at least one MWW type or mordenite type zeolite. The transalkylation unit product stream 52, now containing para-xylene, exits the bottom of the transalkylation unit 48 and may be passed to a benzene column, toluene column, xylene column, para-xylene separation zone, or an isomerization zone.

The acid sites from the MWW zeolites (including MCM-22, MCM-49 UZM-8, and UZM-37 have been removed using oxalic acids and hexafluorosilicates (i e ammonium hexafluorosilicate, AFS).

TABLE 1

| Catalyst: MWW-26/Al2O3, zeolite treated by -> | | As is | Oxalic 1x | Oxalic 2x | Tartaric | Nitric | AFS |
|---|---|---|---|---|---|---|---|
| Toluene conversion, mol % | | 20.0 | 21.8 | 20.9 | 20.6 | 20.4 | 20.5 |
| Aromatics selectivities, mol % | Bz | 0.29 | 0.18 | 0.16 | 0.20 | 0.02 | 0.09 |
| | A8 | 82.81 | 85.09 | 86.90 | 85.97 | 85.26 | 86.59 |
| | A9 | 11.23 | 10.57 | 10.13 | 9.74 | 10.61 | 9.37 |
| | A10 | 1.66 | 1.01 | 0.83 | 0.79 | 0.97 | 0.79 |
| | A11 | 0.36 | 0.17 | 0.13 | 0.11 | 0.14 | 0.12 |
| | HexamethylBz | 0.12 | 0.04 | 0.03 | 0.02 | 0.03 | 0.01 |
| | A12+ | 0.01 | 0.01 | 0.00 | 0.01 | 0.02 | 0.01 |
| | ITN's | 0.01 | 0.01 | 0.00 | 0.01 | 0.01 | 0.01 |
| | DPM's | 3.52 | 2.94 | 1.81 | 3.16 | 2.94 | 3.03 |
| | pX/X | 47.5 | 61.0 | 60.7 | 58.7 | 63.9 | 59.3 |

The data in Table 1 was generated under the operating conditions of a weight hourly space velocity of about 1.37 $hr^{-1}$, a temperature of about 258° C. to about 268° C., and a pressure of about 400 psig. The feed composition is 92.1 wt % toluene, 7.9 wt % methanol. For the sake of clarity, ITN is defined as indanes-tetralins-naphthalenes and DMP is defined as various diphenylmethanes. The results in Table 1 illustrates that compared to un-treated zeolite, the treatments improve the selectivity (desired xylenes selectivity is higher, while un-desired A9+ selectivity is lower), including higher pX/X. Comparison is done at essentially the same toluene conversion, so the selectivity improvement is not due to lower conversion.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

While the invention has been described with what are presently considered the preferred embodiments, it is to be understood that the invention is not limited to the disclosed embodiments, but it is intended to cover various modifications and equivalent arrangements included within the scope of the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process for the methylation of toluene, comprising passing a toluene feed stream and a plurality of methanol feed streams to a reaction zone to produce a reaction zone product stream; separating the reaction zone product stream and passing the reaction zone product stream to a stripper to produce a vent gas stream, an overhead stream comprising toluene and xylenes, a side cut comprising xylenes and a bottoms stream comprising C9+, specifically containing diphenylmethane components; and passing the C9+ stream to a transalkylation zone comprising a transalkylation catalyst comprising at least one MWW zeolite having no acid sites. An embodiment of the invention is one, any or all of prior embodiments in this paragraph up through the first embodiment in this paragraph, wherein the MWW zeolite includes MCM-22. An embodiment of the invention is one, any or all of prior embodiments in this paragraph up through the first embodiment in this paragraph, wherein the MWW zeolite includes MCM-49. An embodiment of the invention is one, any or all of prior embodiments in this paragraph up through the first embodiment in this paragraph, wherein the MWW zeolite includes UZM-8. An embodiment of the invention is one, any or all of prior embodiments in this paragraph up through the first embodiment in this paragraph, wherein the MWW zeolite includes UZM-37. An embodiment of the invention is one, any or all of prior embodiments in this paragraph up through the first embodiment in this paragraph, wherein the acid sites are removed from the MWW zeolite using Al-chelating agents. An embodiment of the invention is one, any or all of prior embodiments in this paragraph up through the first embodiment in this paragraph, wherein the acid sites are removed from the MWW zeolite using steaming. An embodiment of the invention is one, any or all of prior embodiments in this paragraph up through the first embodiment in this paragraph, wherein the Al-chelating agents include organic acids such as oxalic acid, citric acid, tartaric acid, EDTA. An embodiment of the invention is one, any or all of prior embodiments in this paragraph up through the first embodiment in this paragraph, wherein the Al-chelating agents include ammonium hexafluorosilicate. An embodiment of the invention is one, any or all of prior embodiments in this paragraph up through the first embodiment in this paragraph, wherein the Al-chelating agents include hexafluorosilicates with cations other than ammonium alkaline, alkaline earth, or organic (i.e. protonated amine). An embodiment of the invention is one, any or all of prior embodiments in this paragraph up through the first embodiment in this paragraph, wherein the Al-chelating agents include inorganic acids such as nitric acid. An embodiment of the invention is one, any or all of prior embodiments in this paragraph up through the first embodiment in this paragraph, wherein the reaction zone operates at a temperature of at about 200° C. to about 400° C. An embodiment of the invention is one, any or all of prior embodiments in this paragraph up through the first embodiment in this paragraph, wherein the reaction zone operates at a pressure of about 103 kPa (about 15 psig) to about 2758 kPa (about 400 psig). An embodiment of the invention is one, any or all of prior embodiments in this paragraph up through the first embodiment in this paragraph, wherein the reaction zone comprises at least one reactor. An embodiment of the invention is one, any or all of prior embodiments in this paragraph up through the first embodiment in this paragraph, wherein the reaction zone comprises no more than four reactors. An embodiment of the invention is one, any or all of prior embodiments in this paragraph up through the first embodiment in this paragraph, wherein the overhead stream comprising toluene is recycled back to the toluene feed stream. An embodiment of the invention is one, any or all of prior embodiments in this paragraph up through the first embodiment in this paragraph, further comprising separating a methanol stream from the reaction zone product stream and recycling the methanol stream back to the methanol feed stream. An embodiment of the invention is one, any or all of prior embodiments in this paragraph up through the first embodiment in this paragraph, wherein the toluene to methanol molar ratio is between 0.5 and 10. An embodiment of the invention is one, any or all of prior embodiments in this paragraph up through the first embodiment in this paragraph, wherein the toluene conversion is about 10-80%. An embodiment of the invention is one, any or all of prior embodiments in this paragraph up through the first embodiment in this paragraph, wherein the selectivity of para-xylenes to xylenes is about 60-70%. An embodiment of the invention is one, any or all of prior embodiments in this paragraph up through the first embodiment in this paragraph, further comprising at least one of sensing at least one parameter of the process and generating a signal or data from the sensing; generating and transmitting data.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for the methylation of toluene, comprising:
    passing a toluene feed stream and a plurality of methanol feed streams to an alkylation reaction zone comprising at least one treated MWW, UZM-8, or UZM-37 zeolite at alkylation conditions to produce an alkylation reaction zone product stream,
    wherein an untreated MWW, UZM-8, or UZM-37 zeolite is contacted with an Al-chelating agent to remove external acid sites and produce the treated MWW, UZM-8, or UZM-37 zeolite having a lower number of external acid sites, and
    wherein the alkylation reaction conditions comprise a temperature of about 200° C. to about 400° C., and a pressure of about 15 psig to about 400 psig, and an A9 selectivity of 9.37 mol % to 10.61 mol %, and
    wherein the alkylation reaction zone product stream has a ratio of para-xylene to xylenes of 58.7% or more;
    separating the alkylation reaction zone product stream into a vent gas stream, an overhead stream comprising toluene and benzene, a side cut comprising xylenes, and a bottoms stream comprising C9+, containing diphenylmethane; and
    passing the bottoms stream directly to a transalkylation zone.

2. The process of claim 1, wherein the MWW zeolite includes MCM-22.

3. The process of claim 1, wherein the MWW zeolite includes MCM-49.

4. The process of claim 1, wherein the zeolite is UZM-8.

5. The process of claim 1, wherein the zeolite is UZM-37.

6. The process of claim 1, wherein the Al-chelating agent comprises oxalic acid, citric acid, tartaric acid, or EDTA.

7. The process of claim 1, wherein the Al-chelating agent comprises ammonium hexafluorosilicate, alkaline hexafluorosilicates, alkaline earth hexafluorosilicates, or organic hexafluorosilicates.

8. The process of claim 1, wherein the Al-chelating agent comprises an inorganic acid.

9. The process of claim 1, wherein the alkylation reaction zone comprises at least one reactor.

10. The process of claim 1, wherein the alkylation reaction zone comprises no more than four reactors.

11. The process of claim 1, wherein the overhead stream comprising toluene is recycled to the toluene feed stream.

12. The process of claim 1, further comprising:
    separating an aqueous stream comprising methanol from the alkylation reaction zone product stream before separating the alkylation reaction zone product stream into the vent gas stream, the overhead stream, the side cut, and the bottoms stream;
    separating a methanol stream from the aqueous stream; and
    recycling the methanol stream to the methanol feed stream.

13. The process of claim 1, wherein the toluene conversion is about 20%.

14. The process of claim 1, further comprising at least one selected from:
    sensing at least one parameter of the process and generating a signal or data from the sensing; and
    generating and transmitting data.

15. The process of claim 1 wherein the alkylation reaction conditions comprise the temperature of about 258° C. to about 400° C.

16. A process for the methylation of toluene, comprising:
    passing a toluene feed stream and a plurality of methanol feed streams to an alkylation reaction zone comprising at least one treated UZM-8 or UZM-37 zeolite at alkylation reaction conditions to produce an alkylation reaction zone product stream,
    wherein an untreated UZM-8 or UZM-37 zeolite is contacted with an Al-chelating agent to remove external acid sites and produce the treated UZM-8 or UZM-37 zeolite having a lower number of external acid sites,
    wherein the alkylation reaction conditions comprise a temperature of about 200° C. to about 400° C., and a pressure of about 15 psig to about 400 psig, and
    wherein the alkylation reaction zone product stream has an increased ratio of para-xylene to xylenes compared to a product stream from the untreated UZM-8 or UZM-37 zeolite;
    separating the alkylation reaction zone product stream into a vent gas stream, an overhead stream comprising toluene and benzene, a side cut comprising xylenes, and a bottoms stream comprising C9+, containing diphenylmethane; and
    passing the bottoms stream directly to a transalkylation zone.

17. The process of claim 16 wherein the alkylation reaction conditions comprise the temperature of about 258° C. to about 268° C.

18. The process of claim 16, wherein the Al-chelating agent comprises oxalic acid, citric acid, tartaric acid, EDTA, ammonium hexafluorosilicate, alkaline hexafluorosilicates, alkaline earth hexafluorosilicates, or organic hexafluorosilicates or an inorganic acid.

* * * * *